United States Patent [19]

Boger et al.

[11] Patent Number: 4,526,753
[45] Date of Patent: Jul. 2, 1985

[54] MULTIPLE PROFILE REAGENT CARD

[75] Inventors: David L. Boger, South Bend, Ind.; Leighton C. Johnson, Edwardsburg, Mich.; Jerry T. Pugh, Elkhart, Ind.

[73] Assignee: Miles Laboratories, Inc., Elkhart, Ind.

[21] Appl. No.: 511,269

[22] Filed: Jul. 6, 1983

[51] Int. Cl.$^3$ .................. G01N 21/78; G01N 33/52
[52] U.S. Cl. .................. 422/56; 435/805; 436/57
[58] Field of Search .................. 422/56, 57, 58, 66; 435/805

[56] References Cited

U.S. PATENT DOCUMENTS

| | | | |
|---|---|---|---|
| 3,552,929 | 1/1971 | Fields et al. | 422/56 |
| 3,620,678 | 11/1971 | Guigan | 422/66 |
| 3,846,247 | 11/1974 | Kronish et al. | 422/56 X |
| 3,875,044 | 4/1975 | Renn et al. | 422/57 X |
| 3,932,133 | 1/1976 | Ishikawa | 422/55 |
| 4,087,332 | 5/1978 | Hansen | 422/56 X |
| 4,160,646 | 7/1979 | Furutani et al. | 422/56 X |
| 4,218,421 | 8/1980 | Mack, Jr. et al. | 422/56 X |
| 4,301,115 | 11/1981 | Rapkin et al. | 422/56 |

Primary Examiner—Barry S. Richman
Assistant Examiner—Robert J. Hill, Jr.
Attorney, Agent, or Firm—Roger N. Coe

[57] ABSTRACT

A multiple profile reagent card for simultaneously or sequentially performing multiple analyses of analyte is formed by applying ribbons of reagent impregnated matrix material parallel to each other on a substrate and then removing portions of at least the matrix material to create separate matrices along each ribbon of matrix material. The multiple profile reagent card facilitates automatic processing of immunochemical, diagnostic and/or serological tests.

1 Claim, 2 Drawing Figures

MULTIPLE PROFILE REAGENT CARD

BACKGROUND OF THE INVENTION

1. Field of the Invention

The present invention relates to a multiple profile reagent card for conducting immunochemical, diagnostic or serological tests and, more particularly, to such a card which facilitates automated processing of the tests.

The art of analytical chemistry has been greatly advanced since biochemistry began emerging as a primary scientific frontier, requiring increasingly sophisticated analytical methods and tools to solve problems. Likewise the medical profession has lent impetus to the growth of analytical chemistry, with its desiderata of both high precision and speed in obtaining results.

To satisfy the needs of the medical profession as well as other expanding technologies, such as the brewing industry, chemical manufacturing, etc., a myriad of analytical procedures, compositions and apparatus have evolved, including the so called "dip-and-read" type reagent test devices. Reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a reagent test device into a sample of body fluid, such as urine or blood, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular constituent in a test sample, but also an estimate of how much of the constitutent is present. Such test devices provide the physician with a facile diagnostic tool as well as the ability to gage the extent of disease or of bodily malfunction.

Illustrative of such test devices currently in use are products available from the Ames Division of Miles Laboratories, Inc. under the trademarks CLINISTIX, MULTISTIX, KETOSTIX, N-MULTISTIX, DIASTIX, DEXTROSTIX, and others. Immunochemical, diagnostic or serological test devices such as these usually comprise one or more carrier matrices, such as absorbent paper, having incorporated therein a particular reagent or reactant system which manifests a detectable response, e.g., a color change in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the test device with a sample is indicative of the presence of a particular constituent and/or its concentration in the sample. Some of these test devices and their reagent systems are set forth in U.S. Pat. Nos. 3,123,443; 3,212,855; 3,814,668; etc.

Regardless of whether the test device is used for the determination of a biological fluid or the analysis of a commercial or industrial fluid, the normal procedure requires that each test device separately come in contact with the sample or specimen to be tested and then that the test device be visually or instrumentally analyzed. Means have been sought in the art for economically and rapidly conducting multiple tests, especially using automated processing. Prior to the present invention no known system had the capability of achieving the desiderata mentioned above.

The traditional dip-and-read test device can be manufactured at relatively low cost and it is convenient for an individual to use, but it is not well suited for use with highly automated equipment. For automated equipment to be of any advantage, it must result in a benefit with respect to cost, handling, and/or speed of obtaining information.

2. Description Of The Prior Art

Apparatus currently available for instrumentally reading individual reagent strips, such as the SERALYZER reflectance photometer or the CLINITEK reflectance photometer, manufactured and sold by the Ames Division of Miles Laboratories, Inc., Elkhart, Ind., requires that each reagent test device must be manually loaded into the instrument after contacting the test device with specimen or sample to be tested. Manual loading requires that the reagent test device be properly positioned in the instrument within a limited period of time after contacting the solution or substance to be tested. At the end of the analysis, each test device must be removed from the instrument for disposal.

A different format is presently used in the CLINILAB automated urinalysis system, which is manufactured and sold by the Ames Division of Miles Laboratories, Inc., Elkhart, Ind. The CLINILAB instrument uses a cassette containing reagent areas mounted seriatim on a continuous plastic substrate which is wound into a reel and housed in a cassette. While the CLINILAB reagent cassette is well suited for automation, the manufacturing cost for this type of format amounts to eight times that of the dip-and-read test device format mentioned above.

In accordance with the present invention, instrumental testing for immunochemical, diagnostic or serological purposes can be achieved using a multiple profile reagent card comprising multiple reagent impregnated matrices for simultaneously or sequentially performing multiple analyses of analytes. The multiple profile reagent card results in an efficient, economical, rapid and convenient way of performing such analyses.

SUMMARY OF THE INVENTION

An object of the present invention is to provide a multiple profile reagent card for simultaneously or sequentially performing multiple analyses of analytes.

Another object of the present invention is to provide a multiple profile reagent card which permits rapid, economical, efficient and convenient immunochemical, diagnostic or serological testing.

Still another object of the present invention is to provide a multiple reagent card for conducting an immunochemical, diagnostic or serological test using automated equipment.

In accordance with the present invention, a multiple profile reagent card is provided comprising multiple reagent impregnated matrices for simultaneously or sequentially performing multiple analyses of analytes, said reagent card consisting of ribbons of reagent impregnated matrix material applied parallel to each other on a substrate, wherein the reagent impregnated matrix material is cut following application to the substrate so as to provide separated matrices along each ribbon of matrix material.

BRIEF DESCRIPTION OF THE DRAWINGS

Other and further objects, advantages and features of the invention will be apparent to those skilled in the art from the following detailed description thereof, taken in conjunction with the accompanying drawings, in which.

DESCRIPTION OF THE PREFERRED EMBODIMENTS

The multiple profile reagent card forming the subject matter of the present invention is characterized by a substrate film or layer on which ribbons of reagent impregnated matrix material have been applied parallel to each other. The ribbons of matrix material are then cut at suitable intervals to remove a portion of the matrix material and thereby create separated matrices along each ribbon of matrix material. Advantageously, the separated matrices are obtained using a machine which forms a slot in the multiple profile reagent card between each separate matrix.

Figure 1:
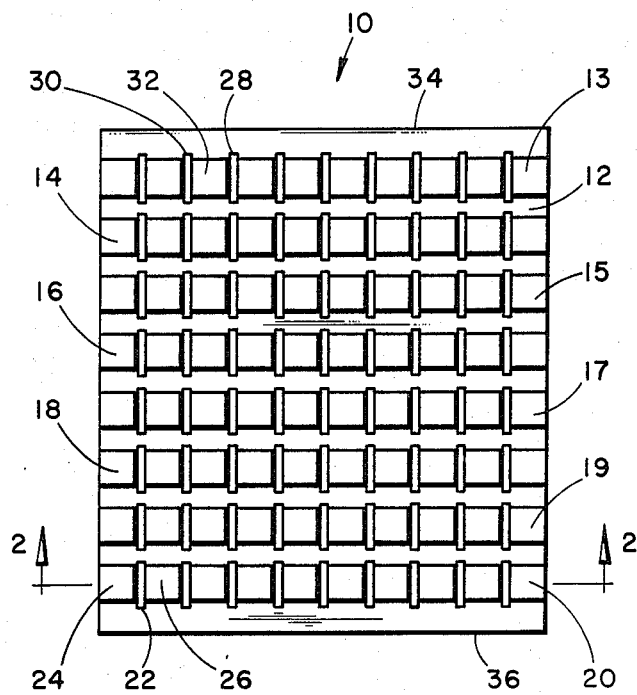
FIG. 1 is top view of a multiple profile reagent card in accordance with the present invention.
Figure 2:
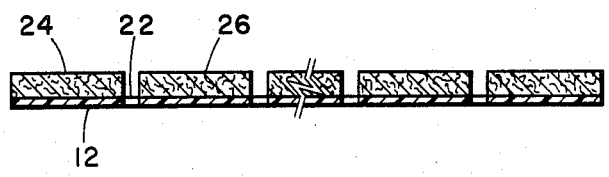
FIG. 2 is a view of the multiple profile reagent card taken along lines 2—2 in FIG. 1.

Turning now to FIGS. 1 and 2 of the drawings, a multiple profile reagent card 10 is shown containing a substrate 12 onto which multiple ribbons of reagent impregnated matrix material 13–20 have been applied parallel to each other. Each ribbon of matrix material is separated into individual matrices by removing a portion of the ribbon matrix material. For example, slots 22 cut through ribbon 20 and through substrate 12 parallel to each other along the length of ribbon 20 result in a series of individual matrices, such as matrices 24 and 26, which are attached to substrate 12. Each of the matrices has the characteristics of the reagent impregnated matrix material which formed ribbon 20 and are capable of providing individual analysis of sample material applied to reagent material forming pads 24 and 26. By similarly removing portions of each ribbon so as to provide a series of individual matrices along each row of reagent impregnated ribbon, a multiple profile reagent card is formed which contains multiple reagent impregnated matrices for simultaneously or sequentially performing multiple analyses of analytes.

The substrate can be formed of any suitable material which is rigid or semirigid and which tends to be nonreactive with the reagents present in the matrix material or with the sample to be tested. Examples of suitable materials include ethylene polymers, propylene polymers, styrene polymers, phenolic polymers, acrylonitrile polymers, methacrylate polymers, etc. Polystyrene is a preferred material. Other, less preferred materials can be used for special instances. For example, cardboard which has been specially treated by a suitable coating to make it water impermeable could be used as a substrate material. Other less preferred materials include metal and glass substrates.

The size of the substrate is not critical and can be made any convenient size. One preferred multiple profile reagent card is illustrated in the drawings in which a different reagent material is present in each of ribbons 13 through 20 and the ribbons are cut so as to provide ten separate matrices for each of the eight ribbons of reagent material present. Accordingly, with respect to the embodiment illustrated in FIGS. 1 and 2, a total of up to 80 separate tests can be performed. The number of profiles or matrices present, can be either increased or decreased, depending on such limitations as ease of handling, convenience, cost, etc.

The reagent ribbons, which are applied to the substrate material, can be any of the materials heretofore suggested for use with dip-and-read reagent test devices.

The matrix utilized in forming the ribbons can take on a multitude of forms. U.S. Pat. No. 3,846,247 teaches the use of felt, porous ceramic strips, and woven or matted glass fibers. Additionally, U.S. Pat. No. 3,552,928 teaches the use of wood sticks, cloth, sponge material, and argillaceous substances. The use of synthetic resin fleeces and glass fiber felts as a carrier matrix is suggested in British Pat. No. 1,369,139. Another British Pat. No. 1,349,623, proposes the use of light-permeable meshwork of thin filaments as a cover for an underlying paper matrix. Polyamide fibers are taught in French Pat. No. 2,170,397. These suggestions notwithstanding, however, the material predominatly used in the art as a matrix, and that which is especially suitable for the present invention, is a bibulous paper such as filter paper. It can thus be seen that there is a great deal of leeway in selecting an appropriate material for use as a carrier matrix, and the matrix can take on various physical forms.

Whichever is chosen, a web of carrier matrix material can be incorporated with the present composition in several ways. The web can be drawn through a solution or suspension of the indicator and enhancer in an appropriate solvent such as water, methanol, benzene, cyclohexane, etc. After drying, the composition-laden matrix web can be fastened to one surface of a substrate material. This can be achieved using a double-faced adhesive tape known as Double Stick, available from the 3M Company.

While the formation of separate matrices along each ribbon of matrix material does not require the removal of any portion of the substrate in addition to the removal of a portion of the matrix material, in the preferred embodiment individual matrices are formed along each ribbon of matrix material by creating a hole or slot through the ribbon of reagent impregnated matrix material. Normally, a corresponding hole or slot will also be formed through the substrate material. For example, in FIG. 1 slots 28 and 30 separate ribbon 13 into separate matrix area 32 which has the same characteristics as other matrices along ribbon 13, but is separated from those matrices such that matrix 32 forms a separate reagent pad area capable of independently performing an analysis of analyte applied to the pad. Any suitable means of forming the holes or slots can be used, including a rotary die, a stamp, a punch, etc. The size or width of the cuts made between adjacent matrices can be varied provided the length of such cuts or slots is sufficient to remove the ribbon of reagent impregnated matrix material between adjacent matrices and further provided the width of the cuts or slots is sufficient to permit individual analyses to be performed on each of the matrix areas without encountering runover problems with sample and reagent material from one matrix to the other.

The format of the multiple profile reagent card lends itself to use in automated equipment since a card can quickly and conveniently be presented for running multiple profiles with multiple tests. Once the card is aligned in the equipment, the card permits simultaneous or sequential analysis of analyte at all or a portion of the matrices present on the multiple profile reagent card. If desired, multiple profile reagent card 10 of FIGS. 1 and 2 could incorporate suitable indexing means such as punched holes (not shown) in substrate material 12 along edges 34 and 36 so as to facilitate the alignment, presentation, and/or sequencing of the multiple profile reagent card through automated instrumentation.

The multiple profile reagent cards of the present invention tend to be inexpensive to manufacture in the preferred format since ribbons of reagent impregnated material normally used in the formation of conventional individual dip-and-read test devices can be utilized to form the reagent cards. A single rolling or punching operation can effectively create the desired number of matrices on each card.

The resulting multiple profile reagent card is disposable and results in less waste then the equivalent number of dip-and-read test devices in that a substantial amount of substrate material normally required for the handle portion of a conventional dip-and-read type test device is not required.

While the illustrated multiple profile reagent card has a more or less rectangular configuration, other suitable configurations, e.g., square, can be used. Moreover, the distant between the ribbons of reagent impregnated matrix material can be varied, if desired. The preferred configuration, however, is illustrated in the drawings since the largest number of matrices can be inserted onto a card of the smallest possible dimensions.

It will also be understood that the size of the matrices need not be uniform. For example, instead of having a square configuration, the matrices can be rectangular in configuration. The width of the reagent ribbon can also be varied.

Because of the configuration of the multiple profile reagent card, such cards can be preloaded into a canister or other holding device and fed automatically into automated photometric apparatus for determining reflectance characteristics of treated reagent areas.

From the foregoing, it will be seen that this invention is well adapted to attain all of the ends and objects hereinabove set forth, together with other advantages which are obvious and inherent to the system. The multiple profile reagent cards of the present invention have the advantages of convenience, simplicity, relatively inexpensiveness, positiveness, effectiveness, durability, accuracy and directness of action. The invention substantially overcomes the problem of effectively and rapidly performing multiple analyses of analytes with automated equipment without adopting a very expensive format. The multiple profile reagent cards provide a very effective way of accurately positioning and transporting multiple reagent impregnated matrices for simultaneously or sequentially performing multiple analyses of analyte. The multiple profile reagent card can be manufactured inexpensively in such a way as to prevent or substantially eliminate runover from occurring between adjacent reagent pads on the same card. Another advantage of the multiple profile reagent cards is that it facilitates contact of the reagent matrices with sample material to be tested as well as the presentation of the sample contacted multiple profile reagent cards to an instrument for performing reflectance measurements, thereby eliminating wasted test devices which sometimes occur with inexperienced users who have not developed a good technique for contacting the specimen to be tested with a reagent test device. Obviously, the use of automated equipment increases the speed which samples can be analyzed and reduces the amount of human intervention required, for example, with an equivalent number of individual, dip-and-read test devices.

Should there be a desire to store the multiple profile reagent cards for a period of time after testing, the cards of the present invention permit a convenient way of storing and retaining test results.

Obviously, many other modifications and variations of the invention as hereinbefore set forth can be made without departing from the spirit and scope thereof.

What is claimed is:

1. A multiple profile reagent card comprising multiple reagent impregnated matrices for simultaneously or sequentially performing multiple analyses of analyte wherein the matrices consist of multiple ribbons of reagent impregnated matrix material positioned parallel to each other on a substrate with slots cut completely through said ribbons and said substrate at spaced locations along each ribbon to define matrices along each ribbon, said ribbons being the same or different, said slots extending perpendicular to the length of the reagent impregnated ribbons to substantially prevent runover between adjacent matrices along each ribbon of matrix material, said ribbons of matrix material being applied in a continuous manner to the substrate and then separated by said slots to produce said matrices.

* * * * *